United States Patent [19]

Schnek et al.

[11] 4,202,884
[45] May 13, 1980

[54] DERIVATIVE OF LYSOZYME

[75] Inventors: Arthur G. Schnek, Brussels; Yvan-Roger-Jean Looze, Wavre; Marc M. Deconinck, Hamme-Mille, all of Belgium

[73] Assignee: Prospa S.A., Brussels, Belgium

[21] Appl. No.: 957,001

[22] Filed: Oct. 31, 1978

[30] Foreign Application Priority Data

Nov. 1, 1977 [GB] United Kingdom ............... 45411/77

[51] Int. Cl.$^2$ ............................................. A61K 37/54
[52] U.S. Cl. ...................................... 424/94; 435/206; 435/188
[58] Field of Search ............... 195/62, 63, 68; 424/94; 435/206

[56] References Cited

U.S. PATENT DOCUMENTS

| | | | |
|---|---|---|---|
| 3,859,435 | 1/1975 | Bruzzese et al. | 424/94 |
| 3,937,815 | 2/1976 | Bruzzese et al. | 424/94 |
| 4,065,354 | 12/1977 | Ullman et al. | 195/63 |

OTHER PUBLICATIONS

Depasse et al. in Environmental Research 12, 371–374 (1976).

*Primary Examiner*—Lionel M. Shapiro
*Attorney, Agent, or Firm*—Wenderoth, Lind & Ponack

[57] ABSTRACT

The present invention provides a new substance derived from the enzymatic polypeptide lysozyme by methylation in the $\epsilon$-position on the amino nitrogen of lysine residues, this new substance being called $\epsilon$-N-trimethyl[1lys]-lysozyme.

3 Claims, No Drawings

DERIVATIVE OF LYSOZYME

BACKGROUND OF THE INVENTION

As is known, lysozymes and especially lysozymes of animal origin, are compact polypeptides with a hydrolase activity [E.C.3.2.1.17], with a net positive charge and with a molecular weight of about 15,000. Slight differences in the polypeptide chain in the number of amino acid residues do not substantially change the biological activity of the enzyme. The lysine residues present in the chain vary from a minimum of 6 in egg white lysozyme to a maximum of 8 in dog lysozyme.

As is well known, any chemical treatment which leads to the loss of the basic feature, such as acetylation, inactivates the enzymes. The presently held opinion is that the $\epsilon$-amino groups of lysine must preserve their basic nature in order that the total biological activity of the molecule is preserved or is only slightly modified. If a chemical transformation results in an increase in the basicity, some of the biological properties may, in theory, be improved.

Animal lysozymes are reasonably stable at acid pH values but unstable at alkaline pH values; they are heat-resistant for some minutes in weakly acidic media, without an appreciable loss of enzymatic activity, this heat stability being due to the number of cystine residues present in the molecule.

From a purely enzymatic point of view, the substrates for enzyme activity of the animal lysozymes are bacterial cell wall mucopeptides and animal and plant chitin: for this reason, they have also been called N-acetyl-muramide glycanohydrolases.

Biologically, lysozymes have a lysing activity on many bacteria, inducing release from the cell walls of immunologically competent amino sugars. In higher organisms, the lysozymes form part of the natural cell and/or humoral immunity systems or, more precisely, of the antibody-completement-properdin system.

That the role of the lysozymes is not limited solely to immune activity and bacterial lysis is suggested by the fact that animals under sterile conditions have the same lysozyme activity at a humoral level as animals under non-sterile conditions. A transglycosylase and a transferase activity has, in fact, been observed which is particularly useful, for example, in the regenerative processes of connective tissues.

The in vivo methylation processes of some amino acids are generally related to specific enzymatic control processes, after genic transcription.

We have found that it is chemically possible to achieve the trimethylation of the lysine contained in the lysozyme polypeptide chain to give the new substance $\epsilon$-N-trimethyl[lys]-lysozyme.

SUMMARY OF THE INVENTION

Thus, the present invention provides a lysozyme derivative in which the $\epsilon$-position on the amino nitrogen of the lysine residues present therein are methylated.

DETAILED DESCRIPTION OF THE INVENTION

Lysozyme is dissolved in a sodium borate buffer and a methylating agent, such as methyl fluorosulphonate, is added portionwise. When the reaction is finished, the solution is percolated through an appropriate resin, for example "Sephadex" G25, and the $\epsilon$-N-trimethyl[lys]-lysozyme freed from other reaction products isolated by lyophilising the eluate.

The new lysozyme derivative thus obtained has a toxicity which is not substantially different from that of native lysozyme. This was demonstrated in some animal species after oral administration.

However, the biological properties of the modified lysozyme molecule were found to be very interesting. These include, in particular, a protective activity of the new lysozyme derivative on erythrocytic haemolysis by silica gel (for a description of the method, referred to other substances, see Depasse and Leonis's test, Environmental Research, 12, 371/1976) in which it was found to be up to 100 times more active than native lysozyme. The tissue-damaging action of silica powder on erythrocytes depends on the fact that, in erythrocyte protoplasm, the inorganic matter finds the physico-chemical conditions required to hydrate and goes into solution in the form of silicic acid, followed by polymerisation to polysilicic acid. The latter causes protoplasmic protein denaturing, with consequent erythrocytolysis. $\epsilon$-N-trimethyl-[lys]-lysozyme neutralises the acid charges of the polysilicic acid more effectively than native lysozyme so that erythrocytic haemolysis is considerably suppressed.

We have also observed that the new lysozyme derivative has a greater degree of tropism towards lipid membranes, using simulated systems of membrane cardiolipin: phosphatidylethanolamine. This could lead to a greater interference activity by the new lysozyme derivative on gram-negative bacteria which, as is known, have lipid components in their cell wall, unlike gram-positive bacteria which lack these complex structures.

The present invention also provides pharmaceutical compositions comprising the new lysozyme derivative, in admixture with a solid or liquid pharmaceutical diluent or carrier.

The following Examples are given for the purpose of illustrating the present invention:

EXAMPLE 1

Lysozyme hydrochloride is dissolved at ambient temperature at a concentration of 10 mg/ml., in a 0.1 M buffer solution of sodium borate with a pH of 9.2. After the enzyme has dissolved, methyl fluorosulphonate is added portionwise up to a mole ratio of 100 moles of reagent per mole of enzyme.

After about 30 minutes, during which the reaction solution is vigorously stirred, the solution is subjected to gel filtration through a resin ("Sephadex" G25), using $10^{-3}$ N acetic acid as eluent.

Subsequently, the $\epsilon$-N-trimethyl[lys]-lysozyme, freed from other reaction products, is obtained by lyophilisation of the eluate; 96% yield.

EXAMPLE 2

50 g. Lysozyme are dissolved in 250 ml of distilled water; 10 ml methyl fluorosulphonate are then added dropwise, with vigourous stirring, over a period of 30 minutes, while keeping the temperature at 0° C. The pH of the reaction mixture is adjusted to 7 by adding 1 N aqueous sodium hydroxide solution. In the course of this pH adjustment, trimethyl lysozyme is seen to precipitate out. The suspension is kept overnight at 4° C. and then centrifuged (43,000 g for 30 minutes). The precipitate is dissolved in 0.001 N hydrochloric acid and finally lyophilised.

The structure of lysozyme and the structure of its trimethylated derivative are very similar, the only difference being the presence of the methyl groups on the ε-amino groups of lysozyme radicals, this similarity of the structure being confirmed by the fluorescence spectra and by the circular dichroism.

The first were measured with a Hitachi-Perkin Elmer spectrophotometer (type MPF 2A) and gave the following results:

| native lysozyme | $\lambda$ excitation maximum = 290 nm |
| --- | --- |
|  | $\lambda$ emission maximum = 340 nm |
| ε-N-trimethyl[lys]-lysozyme | $\lambda$ excitation maximum = 290 nm |
|  | $\lambda$ emission maximum = 342 nm |

The $\lambda$ emission maximum of denatured lysozyme is 350 nm, thus confirming that, following trimethylation of the lysine, the ε-N-trimethyl[lys]-lysozyme obtained does not undergo denaturation or important alterations in the secondary or tertiary structure.

The circular dichroism over a wavelength interval of from 200 to 250 nm confirms that the helicoidal sites and the duplications of the lysozyme derivative do not differ greatly from those of native lysozyme.

The disappearance of the free amino groups of native lysozyme was followed spectrophotometrically after treatment with picrylsulphonic acid.

The absence of lysine residues and the quantitative conversion of these into ε-N-trimethyl lysine was confirmed by the analysis of the amino acid percentage, after total hydrolysis of the polypeptide with 5.6 N hydrochloric acid for 24 hours at 105° C. in a vacuum sealed tube, according to the method of C. G. Zarkadas (Canadian Journal of Biochemistry, 53, 96/1975).

We claim:
1. ε-N-trimethyl[lys]-lysozyme.
2. A process for the preparation of ε-N-trimethyl[lys]-lysozyme, wherein lysozyme is dissolved in a sodium borate buffer and a methylating agent is added thereto portionwise.
3. A pharmaceutical composition, comprising ε-N-trimethyl[lys]-lysozyme, in admixture with a solid or liquid pharmaceutical diluent or carrier.

* * * * *